United States Patent
Bange et al.

(10) Patent No.: US 7,551,965 B2
(45) Date of Patent: *Jun. 23, 2009

(54) SYSTEM AND METHOD FOR REMOVING NARROWBAND NOISE

(75) Inventors: Joseph E. Bange, Eagan, MN (US); Steven Schmitt, Stillwater, MN (US); Fred Schleifer, Prior Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 273 days.

This patent is subject to a terminal disclaimer.

(21) Appl. No.: 11/276,632

(22) Filed: Mar. 8, 2006

(65) Prior Publication Data

US 2006/0142821 A1    Jun. 29, 2006

Related U.S. Application Data

(63) Continuation of application No. 10/649,406, filed on Aug. 27, 2003, now Pat. No. 7,016,739, which is a continuation of application No. 09/754,098, filed on Jan. 4, 2001, now Pat. No. 6,622,044.

(51) Int. Cl.
*A61N 1/08* (2006.01)

(52) U.S. Cl. .................................................. 607/60

(58) Field of Classification Search ............. 607/30–32, 607/59, 60; 128/901, 903; 375/346; 702/189; 600/509
See application file for complete search history.

(56) References Cited

U.S. PATENT DOCUMENTS

| | | | |
|---|---|---|---|
| 4,537,200 A * | 8/1985 | Widrow ....................... | 600/509 |
| 4,562,841 A | 1/1986 | Brockway et al. | |
| 5,058,581 A | 10/1991 | Silvian | |
| 5,107,833 A | 4/1992 | Barsness | |
| 5,136,529 A * | 8/1992 | Makie et al. ................. | 702/189 |
| 5,168,871 A | 12/1992 | Grevious | |
| 5,226,057 A | 7/1993 | Boren | |
| 5,337,756 A | 8/1994 | Barbier et al. | |
| 5,466,246 A | 11/1995 | Silvian | |
| 5,562,713 A | 10/1996 | Silvian | |
| 5,630,836 A | 5/1997 | Prem et al. | |
| 5,683,432 A | 11/1997 | Goedeke et al. | |
| 5,741,315 A | 4/1998 | Lee et al. | |
| 5,843,139 A | 12/1998 | Goedeke et al. | |
| 5,960,091 A | 9/1999 | White et al. | |
| 5,999,857 A | 12/1999 | Weijand et al. | |
| 6,020,783 A | 2/2000 | Coppola | |
| 6,052,420 A * | 4/2000 | Yeap et al. ................... | 375/346 |
| 6,201,993 B1 | 3/2001 | Kruse et al. | |
| 6,426,983 B1 | 7/2002 | Rakib et al. | |
| 6,556,871 B2 | 4/2003 | Schmitt et al. | |
| 6,622,044 B2 | 9/2003 | Bange et al. | |
| 7,016,739 B2 | 3/2006 | Bange et al. | |
| 2003/0199939 A1 | 10/2003 | Schmitt et al. | |

OTHER PUBLICATIONS

Guidant, "CONTAK TR CHFD Model 1241", *System Guide*, Congestive Heart Failure Device,(1999),1-191.

(Continued)

*Primary Examiner*—Angela D. Sykes
*Assistant Examiner*—George Manuel
(74) *Attorney, Agent, or Firm*—Schwegman, Lundberg & Woessner, P.A.

(57) ABSTRACT

A system and method for removing narrowband noise from an input signal in which notch filters having notch frequencies corresponding to the noise are dynamically adjusted in accordance with a detected noise spectrum. The method may be applied to telemetry systems for implantable medical devices such as cardiac pacemakers to result in improved noise immunity.

20 Claims, 3 Drawing Sheets

OTHER PUBLICATIONS

Medtronic, "INSYNC III Device Model 8042", *Device Programming Guide*, INSYNC III Device Model 8042, Vision Programmer Software Model 9981,(2000),1-260.

Medtronic, "INSYNC III Device Model 8042", *Device Reference Guide*, INSYNC III Device Model 8042, Vision Programmer Software Model 9981,(2002),1-252.

St. Jude Medical, "Atlas + HF Models V-343, V-341", *User's Manual*, Implantable Cardioverter-Defibrillator,(Sep. 2003),1-30.

St. Jude Medical, "Epic HF Model V-339", *User's Manual*, Implantable Cardioverter-Defibrillator,(Jul. 2002),1-26.

St. Jude Medical, "Model 3510 Programmer with Model 3307 Software", *Reference Manual*, For Atlas, Atlas+, Epic, Epic+, Photon u and Photon Implantable Cardioverter/Defibrillators,(Sep. 2003),1-314.

\* cited by examiner

SYSTEM AND METHOD FOR REMOVING NARROWBAND NOISE

CROSS-REFERENCE TO RELATED APPLICATION(S)

This application is a continuation of U.S. patent application Ser. No. 10/649,406, filed on Aug. 27, 2003, now issued as U.S. Pat. No. 7,016,739, which is continuation of U.S. patent application Ser. No. 09/754,098, filed on Jan. 4, 2001, now issued as U.S. Pat. No. 6,622,044, the specifications of which are incorporated herein by reference.

FIELD OF THE INVENTION

This invention pertains to methods and systems for removing noise from signals. The invention finds particular application to telemetry systems used in implantable medical devices such as cardiac pacemakers and implantable cardioverter/defibrillators.

BACKGROUND

Implantable medical devices, including cardiac rhythm management devices such as pacemakers and implantable cardioverter/defibrillators, typically have the capability to communicate data with a device called an external programmer via a radio-frequency telemetry link. One use of such an external programmer is to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data which may typically be telemetered from an implantable device are various operating parameters and physiological data, the latter either collected in real-time or stored from previous monitoring operations.

Noise refers to any unwanted signal that interferes with the transmission and processing of data signals in a communications system. Such noise may arise from sources either internal or external to the system. Because of limited energy storage capability, implantable medical devices must necessarily transmit their data with a low signal energy, making the transmissions very susceptible to interference from noise. This means that an external programmer can only be satisfactorily used to receive data in relatively noise-free environments. Because of the widespread nature of electromagnetic noise sources, such a constraint may not only be inconvenient to the patient and clinician, but could also be hazardous in an emergency situation. Both broadband and narrowband noise sources contribute to the problem, with modern CRT monitors being a particularly common source of narrowband noise.

SUMMARY OF THE INVENTION

The present invention relates to a system and method for removing narrowband noise from a received signal. In a particular embodiment, after digitizing the received signal, narrowband noise is removed from the input signal samples with a series of notch filters having center notch frequencies generated adaptively so that the notch frequencies match the frequency peaks of a detected noise spectrum. The noise spectrum is detected by first computing a power spectrum of the input signal and then subtracting from it a template spectrum corresponding to an expected input signal without noise. A template spectrum is computed from a representative input signal generated by receiving a transmitted signal under noise-free conditions so that when it is subtracted from the input signal spectrum, the result approximates the power spectrum of the narrowband noise alone. In order to produce a detected noise spectrum that most closely approximates the true noise spectrum, the template spectrum is scaled by a factor that reduces the total power in the detected noise spectrum to a minimal value. The frequency peaks in the detected noise spectrum are then identified and used to synthesize filters with corresponding notch frequencies to remove the noise from the input signal.

The narrowband noise removal method may be employed in a system and method for receiving telemetry data from an implantable medical device to result in an improved capability for operating in noisy environments. In an exemplary system, the transmitted signal from the implantable device is a radiofrequency carrier waveform modulated with digitally encoded data in the form of transmit pulses. Further noise immunity may be provided to the system by matched filtering of the input signal samples and adaptive pulse detection.

DETAILED DESCRIPTION

Figure 1:
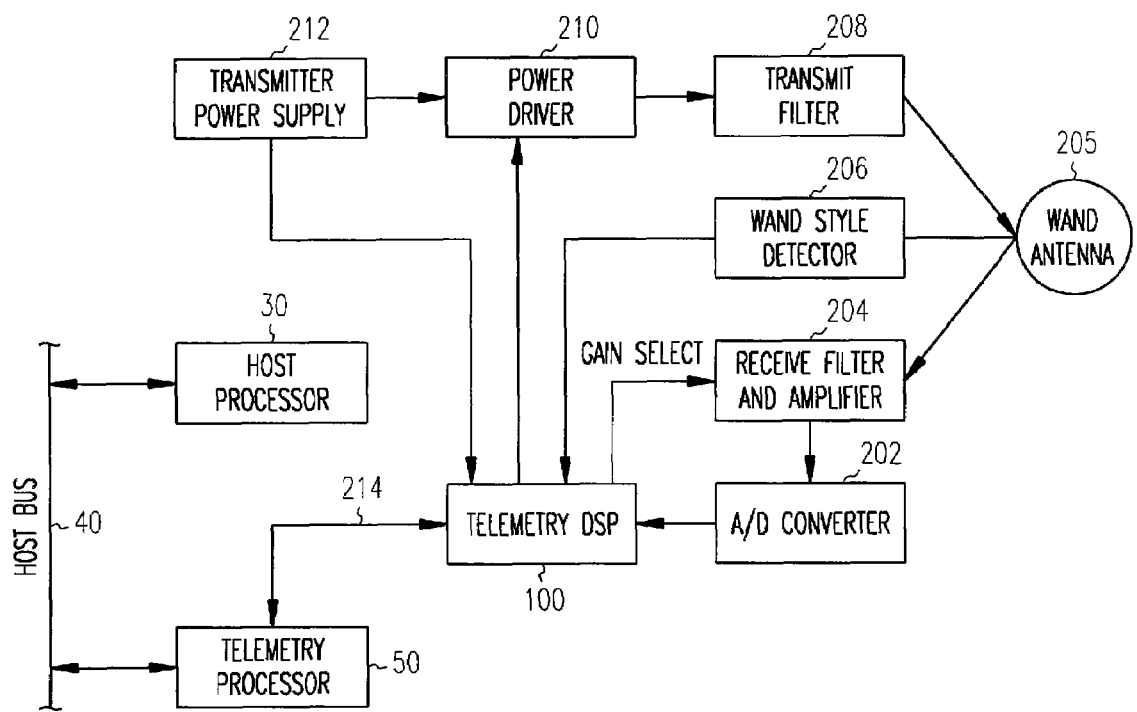
FIG. 1 is a diagram of a telemetry system for an external programmer.

Narrowband noise, such as that generated by certain electronic devices, is bandwidth-limited noise having a power spectrum with characteristic frequency peaks. Thus, a series of notch or bandstop filters with notch frequencies that correspond to those characteristic frequency peaks will remove the narrowband noise from an input signal in real time. Because the power spectrum of narrowband noise found in the environment is not constant, however, successful removal of such noise requires that the notch frequencies adapt to a changing noise spectrum. In accordance with the invention, a power spectrum corresponding to noise present within an input signal is detected by subtracting a template spectrum from the power spectrum of the input signal. The detected noise spectrum is then used to synthesize the notch filters that remove the noise from the input signal. By continuously or periodically detecting a noise spectrum from the input signal, the notch filters can be resynthesized with updated notch frequencies in near real-time to adaptively remove noise from the input signal in response to a changing noise spectrum.

The present invention can be applied to a telemetry data receiving system for an external programmer to result in improved performance in the presence of noise. Telemetry systems for implantable medical devices utilize radio-frequency energy to enable bidirectional communication between the implantable device and an external programmer. An exemplary telemetry system for an external programmer and a cardiac pacemaker is described in U.S. Pat. No. 4,562,841, issued to Brockway et al. and assigned to Cardiac Pacemakers, Inc., the disclosure of which is hereby incorporated by reference. A radio-frequency carrier is modulated with digital information, typically by amplitude shift keying where the presence or absence of pulses in the signal constitute binary symbols or bits. The external programmer transmits and receives the radio signal with an antenna incorporated into a wand which can be positioned in proximity to the implanted device. The implantable device transmits and receives the radio signal by means of an antenna, such as may be formed by a wire coil wrapped around the periphery of the inside of the device casing. As aforesaid, the limited energy storage capability of a typical cardiac rhythm management device necessitates that the signals transmitted from the implantable device be of low energy, thus decreasing the signal-to-noise ratio of the signal received by the external programmer.

In a particular implementation of a telemetry system, data generated by the implantable device is transmitted in the form of a carrier signal modulated with transmit pulses representing the encoded data. The received signal is digitized into input signal samples, and noise is removed from the samples by two filtering operations implemented in the digital signal processor, one for narrowband noise and the other for broadband noise. A series of infinite impulse response (IIR) notch filters is used to remove narrowband noise from the transmitted signal with the filter coefficients dynamically generated in accordance with a detected narrowband noise spectrum. (Other embodiments may utilize FIR or analog filters to remove the narrowband noise.) A finite impulse response (FIR) matched filter then correlates the input signal with a signal corresponding to a transmit pulse in order to remove broadband noise. (In other embodiments, matched filtering can be performed with an IIR or analog filter.) Further noise immunity is provided by dynamically adjusting the threshold at which pulses are detected from the output of the matched filter in accordance with measured noise and signal peaks.

FIG. 1 is a block diagram of the telemetry system of an external programmer. The telemetry processor 50 supervises the operation of the telemetry system, processes the data generated by it, and handles protocol functions such as timing, serial-parallel conversions, and cyclic redundancy code (CRC) checks. The telemetry processor 50 communicates with the main host processor 30 of the programmer over a host bus 40. The telemetry digital signal processor (DSP) 100 performs most of the basic processing functions for the telemetry system. It controls the transmitter, monitors the ambient noise level, and may perform some protocol functions. As described below, the DSP 100 is also responsible for matched filtering of the input samples, creating optimal notch filters for removing narrowband noise in the local noise environment, and dynamically adjusting the threshold signal level at which pulses are detected. A configuration and status channel 214 between the DSP and telemetry processor allows the telemetry processor to configure the telemetry system for a particular implantable device, monitor the received signal strength, set automatic or fixed transmitter polarities, read the wand status (i.e., presence and type), and update the DSP firmware.

The transmitter portion of the telemetry system is controlled by the DSP and includes a transmitter power supply 212, a power driver 210, and a transmit filter 208. The transmitter power supply provides voltages that are compatible with the telemetry wand antenna and provides adjustability of the transmit power by the DSP. The power driver is controlled by the DSP and generates square waves that minimize interference with surface ECG and pace detection. The transmitter filter removes high-frequency components of the power driver's waveform that may cause radiative interference with other devices. A wand antenna 205 is used for both transmitting and receiving signals. The wand style detector 206 senses both the presence of a wand and the wand type by measuring the resistance of a wand identification resistor. This allows the telemetry system to adjust the transmitter and receiver as necessary for particular types of wand antennas. The detector also causes the system to disable the transmitter if the wand is disconnected. The analog portion of the receiving circuitry includes a filter/amplifier 204 that amplifies signals received by the wand as necessary and applies the low-pass anti-aliasing filtering to the signal prior to analog-to-digital conversion by analog-to-digital converter 202. The DSP controls the filter/amplifier's overall gain to adjust for the responses of different types of wands.

Figure 2:
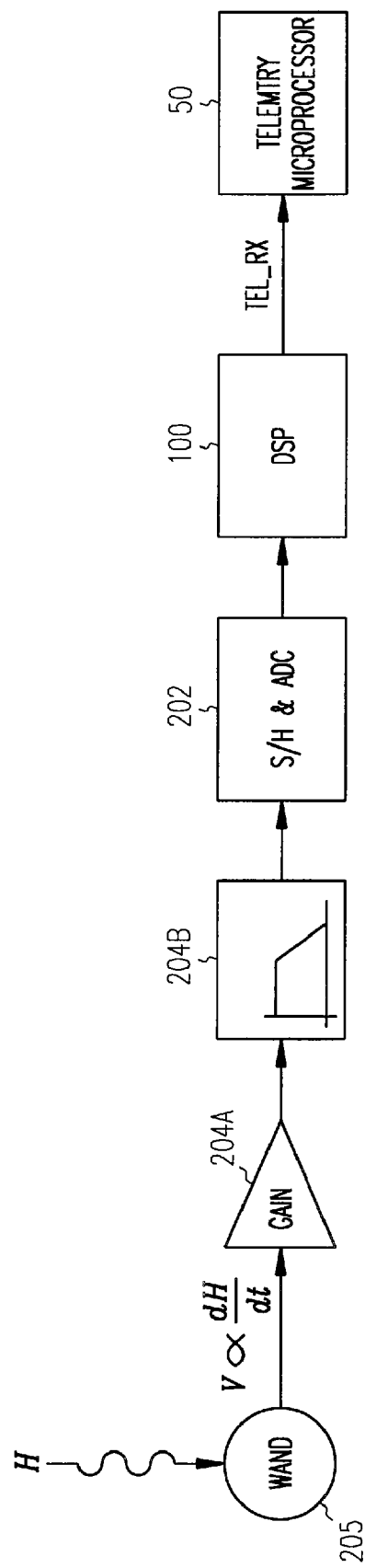
FIG. 2 is a diagram of the receiver portion of the telemetry system.

FIG. 2 is a block diagram of the components making up the receiver portion of the telemetry system. The wand antenna 205 transduces a changing magnetic field intensity to a voltage which is the input signal to the analog receiver circuitry. The filter/amplifier 204 includes gain circuitry 204a that is distributed throughout the receiver and is controllable by the DSP, and a filter 204b that provides an anti-aliasing function with its poles distributed throughout the analog receiver circuitry. In an exemplary embodiment, a 100 KHz carrier signal is ASK modulated with a pulse train sub-carrier encoded with digital data, and the transmit pulses occur at a typical rate of 4 KHz with a pulse width between 20 and 100 microseconds, resulting in a bandwidth of the modulated carrier of approximately 10 to 150 KHz. In order to digitally demodulate the carrier waveform, the analog-to-digital converter must then sample the received signal at a rate at least equal to the Nyquist frequency of 300 KHz. In order to provide good correlation peaks in the matched filter used to detect transmit pulses and to simplify the DSP code, the analog-to-digital converter should preferably sample at a somewhat higher rate (e.g., approximately 350-400 KHz). The resolution of the analog-to-digital converter should also be at least 10 bits in order to provide dynamic range without an automatic gain control circuit. In an exemplary embodiment, a 150-kHz, seventh-order Butterworth filter provides the anti-aliasing function prior to sampling, and a 10-bit analog-to-digital converter 202 with integrated sample and hold generates the input samples. A feedback mechanism within the analog receiver regulates a voltage bias to the receiver input which tends to remove any low frequency components from the input signal. The output of the analog-to-digital converter is a synchronous serial data stream which is sent to the DSP, and the DSP controls the sample rate of the analog-to-digital converter.

Figure 3:
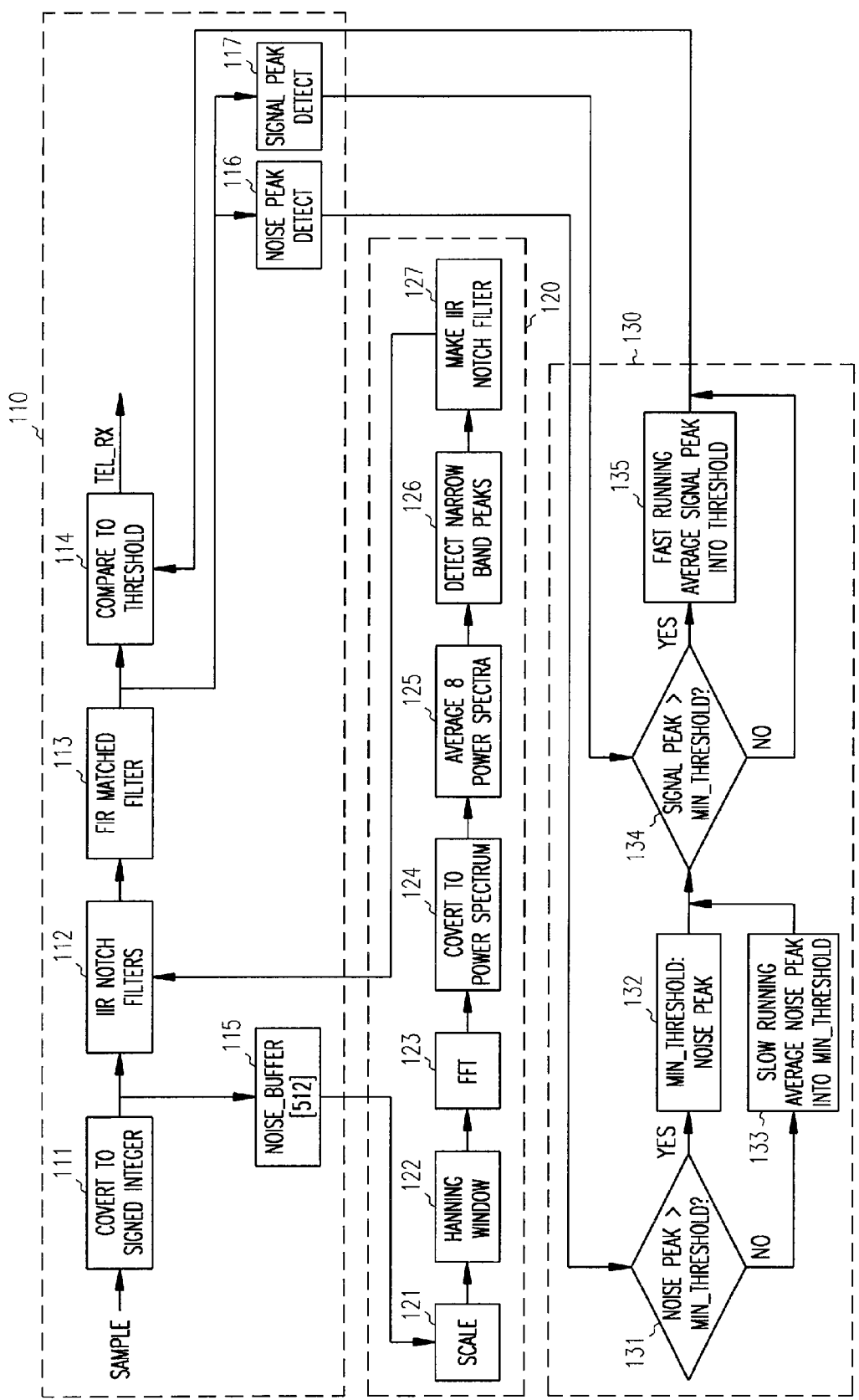
FIG. 3 is a diagram of the signal processing functions performed by the receiver.

FIG. 3 is a block diagram of the functions performed by the digital signal processor 100. When the DSP receives a sample from the ADC, an interrupt is generated. The receiver interrupt handler 110 executed by the DSP processes the samples in the time domain with notch filters 112 and a FIR matched filter 113, digitizes the presence or absence of transmit pulses via pulse detector 114, and then sends this digital data signal TEL_RX to the telemetry microprocessor 50. The receiver interrupt handler also fills a 512 element noise buffer 115 with consecutive raw input samples. When this buffer is filled, the filter generator task 120 processes the buffered data to generate new notch filter coefficients. The receiver interrupt handler then uses these coefficients to adaptively filter out narrowband noise. A noise peak detector 116 and a signal peak detector 117 detect and save peak signal values and peak noise values, respectively. These peak values are periodically processed by the threshold adjustment task 130 in order to adaptively set the threshold that the pulse detector 114 uses to digitize the serial stream.

An integer conversion routine 111 initially subtracts an offset from the input sample to convert the sample from an unsigned integer to a signed integer and remove any bias added by the analog receiver. The sample is then processed through a six biquad IIR filter 112. Each biquad is either a notch filter or a simple pass-through function so that zero to six notch filters may be active at any time. The purpose of the notch filters is to remove narrowband noise from the input signal samples. Since the presence and frequency of this noise depends on the ambient environment, the notch filter coefficients are adaptively generated in response to detected narrow band noise. The filter generator task 120 does this by processing the raw input data in the buffer 115 and periodically updating the IIR filter coefficients.

In order to obtain an optimum frequency response characteristic, the notch filters in this implementation are recursive filters (i.e., infinite impulse response) with adaptively generated filter coefficients so that the notch frequencies match the frequency peaks of a detected noise spectrum. The noise spectrum is detected by first computing a power spectrum of the input signal. The receiver interrupt handler 110 fills a 512 element buffer 115 with consecutive raw input samples. When this buffer is full, this task then scales the buffer values up to limit round-off noise in later calculations at block 121, applies a windowing function such as a Hamming window to the data to limit spectral spreading at block 122, and then discrete Fourier transforms the time domain data into frequency domain data via a Fast Fourier Transform (FFT) algorithm at block 123. The FFT output is then transformed into a power spectrum by taking the norm of the FFT output at block 124. The receiver interrupt handler then fills the buffer again, and the mean of eight consecutive power spectra is taken by block 125. This average power spectrum is then processed by noise spectrum detector 126 in order to detect narrow band noise peaks by subtracting from it a template spectrum corresponding to an expected input signal without noise. A template spectrum is pre-computed from a representative input signal generated under noise-free conditions so that when it is subtracted from the input signal spectrum, the result approximates the power spectrum of the narrowband noise alone. In order to produce a detected noise spectrum that most closely approximates the true noise spectrum, the template spectrum is scaled by a factor that reduces the total power in the detected noise spectrum to a minimal value. The frequency peaks in the detected noise spectrum are then identified and used to synthesize filters with corresponding notch frequencies to remove the noise from the input signal. The notch filters are synthesized with well-known filter synthesis algorithms by filter synthesizer 127.

An exemplary implementation of the filter coefficient updating method just described is as follows. Let $P_i$ be the power spectrum of the input signal and $P_e$ be the template spectrum corresponding to the noise-free signal. The detected noise spectrum $P_n$ is then computed as:

$$P_n = P_i - R * P_e$$

where R is a scaling factor chosen to minimize $P_n$. As a first approximation, R is set to a ratio of $P_i$ to $P_e$ computed by dividing $P_i$ by $P_e$ for each frequency bin, totaling up these ratios, and taking the average ratio. A successive approximation approach is then used to find the optimal scaling factor. First, values for R are found that produce a positive $P_n$ and a negative $P_n$, referred to as R+ and R−, respectively. Since between these two values is the value of R that minimizes $P_n$, new values for R are computed as the average of R+ and R−. As each new R value is tried in the above equation, it replaces the previous value of R+ or R− according to whether $P_n$ is made negative or positive, respectively. The procedure is iterated until the optimal value of R is found to result in the noise spectrum $P_n$. Spectral threshold values for setting the notch filter coefficients are determined by computing the mean and standard deviation of the spectrum $P_n$. In a preferred embodiment, the spectral thresholds are then set at three standard deviations above the mean. These spectral thresholds then constitute the frequency peaks used to set the notch frequencies of the notch filters 112.

Referring to block 110 of FIG. 3, the output of the notch filter stage is input to the FIR matched filter 113. The coefficients of the FIR matched filter 113 are designed to correlate the filtered input signal samples with samples that would be expected from a transmit pulse generated by the implantable device. This type of filter is very effective in discriminating transmit pulses from background noise and increases the range of the telemetry system. The FIR coefficients are derived by capturing a strong, noise-free transmission signal from the implantable device immediately after the samples are converted to signed integers in the receiver interrupt handler. The captured data is then manipulated so that the signal samples are reversed in their order, thus flipping them in time, and each sample is amplitude offset so the average of the samples is near zero in order to eliminate any DC component from the coefficients. The samples are then normalized so that they are fractions, with the maximum sample amplitude equal to 1.0. These fractions are then scaled so the results are in the range of −32768 to 32767 and then copied into the appropriate FIR coefficient table. With these FIR filter coefficients, the FIR matched filter 113 performs a convolution between the input signal samples and samples corresponding to a time-reversed version of the transmit pulse expected to be generated by the implantable device, which is equivalent to performing a cross-correlation between the input signal and a transmit pulse. The output of the FIR matched filter 113 is then compared to a threshold value (td_threshold) by the pulse detector 114. The TEL_RX signal is set high if the filtered value is above td_threshold, otherwise TEL_RX is set low.

The FIR filter output noise and signal peak values are calculated by peak detectors 116 and 117 which are then saved for processing by the threshold adjustment task 130. Signal values are discriminated from noise values based on the timing of the sampled data relative to the last transmit pulse. If a sample occurs at a time when the telemetry protocol does not allow a transmit pulse from the implantable device, then the sample is assumed to be noise, otherwise it is assumed to be a signal. These peak values are periodically processed by the threshold adjustment task 130 in order to adaptively set the value of td_threshold that the pulse detector 114 uses to digitize the serial stream.

The threshold adjustment task 130 uses the peak noise and signal values calculated by the receiver interrupt handler to update the value of td_threshold. The threshold is dynamic so that best spurious noise rejection is accomplished in noisy environments and maximum sensitivity is accomplished in noise-free environments. A local variable, min_threshold, is maintained. This variable is used to set a lower limit to the value of td_threshold. It can rapidly increase in value, but can only slowly decrease in value. If the noise peak is greater than min_threshold as determined at step 131, then min_threshold is assigned the noise peak value at step 132. This is done so that spurious noise which makes its way through the digital filters can be rapidly responded to. Note that Gaussian noise will statistically attain very large values on rare occasions, so min_threshold will track to the Gaussian noise peaks, not the average level. If the noise peak is not greater than min_threshold, then the peak value is averaged into min_threshold using a weighted moving average at step 133. The peak value is lightly weighted, so that the decay rate of min_threshold is relatively slow. This slow averaging is done because min_t-hreshold is designed to guard against spurious noise conditions (i.e., noise absent over a short interval does not necessarily mean the noise has gone away).

The signal peak is then compared to min_threshold at step 134. If it is below min_threshold, then a transmitted signal is assumed to be absent, and td_threshold simply remains at its current value. If the signal peak is above min_threshold, then the signal peak value is averaged into a local store using a weighted moving average at step 135. The value of td_threshold is then set to half the value of this local store. Thus, the value of td_threshold tends to be one half the value of the transmit pulse peak value. The signal peak is weighted relatively heavily, so that td_threshold can react to variations in telemetry range that normally occur as the operator manipulates the wand. Note that if the calculated value of td_threshold is below min_threshold, then td_threshold is clamped to the value of min_threshold. Also, although it is desirable to rapidly change td_threshold in order to react to range variations, it is not desirable for it to change too quickly. Since the matched filtered transmit pulses have a finite slope, the threshold at which a signal is detected will affect the time at which the digitized output changes state. Since the time domain FIR filter output tends to have a shape similar to a Sinc function, rapid variations in td_threshold could detect only the main lobe for some data bits, and leading side lobes for other data bits. Certain synchronization protocols are particularly sensitive to this problem, since they use an alignment bit to establish the data window timing for the subsequent data bits. The threshold should therefore preferably be stable from when the alignment bit is detected to when the last data bit is detected. Thus, the averaging weight of the peak signal is preferably chosen to achieve the best compromise between responsiveness to range variation and threshold stability during receipt of transmitted word.

In the embodiments of the invention described above, the received signal was digitized and processed in the digital domain to derive the transmit pulses. In other embodiments, the received signal could be processed in the analog domain to remove broadband and narrowband noise, correlate the signal with a transmit pulse by matched filtering, and detect transmit pulses with an adaptive threshold.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A system for receiving data from an implantable medical device, comprising:
   an antenna for receiving a signal transmitted from the implantable device;
   circuitry for computing a spectrum of the received signal;
   circuitry for detecting a noise spectrum of the received signal by subtracting a template spectrum from the spectrum of the received signal, the template spectrum representing a noise-free signal;
   circuitry for scaling the template spectrum such that the signal power of the noise spectrum is minimized;
   circuitry for identifying frequency peaks in the noise spectrum in accordance with spectral thresholds derived from the signal power of the noise spectrum;
   one or more notch filters for removing noise from the received signal, the notch filters having notch frequencies corresponding to frequency peaks of the detected noise spectrum;
   a filter generator for updating filter coefficients of the notch filters so that the notch frequencies correspond to the detected noise spectrum.

2. The system of claim 1 wherein the filter generator is configured to set the notch frequencies of the notch filters to match those spectral components of the noise spectrum that exceed a specified spectral threshold value.

3. The system of claim 2 wherein the specified spectral threshold value is calculated as a specified number of standard deviations from the mean of the noise spectrum.

4. The system of claim 1 wherein the filter coefficients of the notch filters are periodically updated by the filter generator.

5. The system of claim 4 wherein the filter coefficients of the notch filters are updated based upon samples of the received signal that are continuously input into a buffer.

6. The system of claim 1 wherein the notch filters are digital infinite impulse response filters synthesized with notch frequencies corresponding to the detected noise spectrum.

7. The system of claim 1 wherein the circuitry for computing a spectrum of the received signal is configured to do so by sampling the received signal and discrete Fourier transforming the samples to produce a power spectrum of the received signal.

8. The system of claim 7 wherein the spectrum of the received signal is produced by summing the power spectra of a series of transformed sample sets of the received signal.

9. The system of claim 1 wherein the circuitry for identifying frequency peaks in the noise spectrum derives spectral thresholds in accordance with the mean and standard deviation of the noise spectrum.

10. The system of claim 9 wherein the circuitry for detecting the noise spectrum is configured to compute the noise spectrum as:

$$P_n = P_i - R * P_e$$

where $P_i$ is the power spectrum of the received signal, $P_e$ is the template spectrum corresponding to the noise-free signal, and R is a scaling factor chosen to minimize $P_n$.

11. A method for receiving data from an implantable medical device, comprising:
    receiving a signal transmitted from the implantable device;
    computing a spectrum of the received signal;
    detecting a noise spectrum of the received signal by subtracting a template spectrum from the spectrum of the received signal, the template spectrum representing a noise-free signal;
    scaling the template spectrum such that the signal power of the noise spectrum is minimized;
    identifying frequency peaks in the noise spectrum in accordance with spectral thresholds derived from the signal power of the noise spectrum;
    removing noise from the received signal with one or more notch filters, the notch filters having notch frequencies corresponding to frequency peaks of the detected noise spectrum;
    updating filter coefficients of the notch filters so that the notch frequencies correspond to the detected noise spectrum.

12. The method of claim 11 further comprising setting the notch frequencies of the notch filters to match those spectral components of the noise spectrum that exceed a specified spectral threshold value.

13. The method of claim 12 wherein the specified spectral threshold value is calculated as a specified number of standard deviations from the mean of the noise spectrum.

14. The method of claim 11 further comprising periodically updating the filter coefficients of the notch filters.

15. The method of claim 14 further comprising periodically updating the filter coefficients of the notch filters based upon samples of the received signal that are continuously input into a buffer.

16. The method of claim 11 wherein the notch filters are digital infinite impulse response filters synthesized with notch frequencies corresponding to the detected noise spectrum.

17. The method of claim 11 further comprising sampling the received signal and discrete Fourier transforming the samples to produce a power spectrum of the received signal.

18. The method of claim 17 further comprising summing the power spectra of a series of transformed sample sets of the received signal.

19. The method of claim 11 further comprising identifying frequency peaks in the noise spectrum by deriving spectral thresholds in accordance with the mean and standard deviation of the noise spectrum.

20. The method of claim 19 further comprising computing the noise spectrum as:

$$P_n = P_i - R^* P_e$$

where $P_i$ is the power spectrum of the received signal, $P_e$ is the template spectrum corresponding to the noise-free signal, and R is a scaling factor chosen to minimize $P_n$.

* * * * *